US005578312A

United States Patent [19]
Parrinello

[11] Patent Number: 5,578,312
[45] Date of Patent: Nov. 26, 1996

[54] SKIN CARE SYSTEM AND METHOD FOR IMPROVING MOISTURE RETENTION IN SKIN

[76] Inventor: Vincene M. Parrinello, 1423 Amor Pl., Escondido, Calif. 92027

[21] Appl. No.: 357,104

[22] Filed: Dec. 15, 1994

Related U.S. Application Data

[63] Continuation-in-part of Ser. No. 57,309, May 5, 1993, abandoned.

[51] Int. Cl.⁶ .............................. A61K 7/00; A61K 7/48
[52] U.S. Cl. .................. 424/401; 424/195.1; 514/847
[58] Field of Search ..................... 424/195.1, 401, 424/74; 514/738, 847

[56] References Cited

U.S. PATENT DOCUMENTS

| | | | |
|---|---|---|---|
| 4,581,230 | 4/1986 | Grollier et al. | 424/74 |
| 4,767,618 | 8/1988 | Grollier et al. | 424/74 |
| 4,880,621 | 11/1989 | Grollier et al. | 424/74 |
| 4,942,033 | 7/1990 | Aubert et al. | 424/195.1 |
| 4,942,153 | 7/1990 | Fernandez | 514/2 |
| 4,948,583 | 8/1990 | Grollier et al. | 424/195.1 |

FOREIGN PATENT DOCUMENTS 0102809  6/1982  Japan .

*Primary Examiner*—Sallie M. Gardner
*Attorney, Agent, or Firm*—Brown, Martin, Haller & McClain

[57] ABSTRACT

The skin care system of the present invention incorporates mixtures of water, dried herbs, leaves, fruits, roots and/or flowers, plant extracts and oils with non-irritating lipids, binders, surfactants, emulsifiers and preservatives. Spring mineral water is the basis of all moisturizing compositions within the inventive skin care system, with the active ingredients being incorporated into the solution by boiling the ingredient in water, as if making a tea. The tea solution may be used alone or combined with ingredients to create moisturizing lotions.

6 Claims, No Drawings

SKIN CARE SYSTEM AND METHOD FOR IMPROVING MOISTURE RETENTION IN SKIN

This is a continuation-in-part of application Ser. No. 08/057,309, filed May 5, 1993, now abandoned.

BACKGROUND OF THE INVENTION

A wide variety of over-the-counter products are available for skin cleansing and moisturizing which are addressed to anything from relieving dry skin to allegedly removing wrinkles. Many of these products claim to be hypoallergenic and non-irritating to most users, however, these products nonetheless contain ingredients that can be irritating or even harmful to individuals who, for some reason, have become highly sensitized to certain chemicals in the skin care products.

A large part of the group which possesses this extreme sensitivity is made up of individuals with illnesses such as cancer, AIDS, anorexia and other eating disorders, and individuals who are undergoing hormone treatment. For cancer and AIDS patients who are undergoing chemotherapy or radiation treatment, or who are receiving other intensive treatments, some of the side effects of these treatments are extremely dry skin, poor and uneven skin tone, and increased sensitivity to certain chemicals which might be contained in most skin care compositions. For individuals with eating disorders, poor nutrition and chemical changes in the body result in, among other things, very dry skin and poor skin tone.

An individual's skin reflects their emotional state of mind as well as their physical condition. In recent years it has been observed that the psychological well-being of an individual who is undergoing treatment for a life threatening illness is an important factor in their recovery. Improvement of the individual's feeling of self-worth and ability to fit in and feel comfortable being with other people can all help in boosting their sense of well-being. However, while it would be desirable to attempt to make the person feel good about themselves by providing skin care products and cosmetics to counter the skin drying and damage which affects their appearance, the products currently on the market may actually exacerbate the individual's low esteem by causing an irritating reaction which emphasizes the distorted self-image that the individual is different and that the difference is obvious to anyone who sees the individual.

SUMMARY OF THE INVENTION

It is an advantage of the present invention to provide a skin care system which is particularly suited to the sensitivities of individuals who are undergoing treatment for life threatening illnesses.

It is a further advantage of the present invention to provide a skin care system which avoids petroleum derivatives, solvents and alcohols which can create an adverse reaction by the user's skin.

Still another advantage of the present invention is to provide a method for rehydrating and moisturizing the skin.

The skin care system and method of the present invention incorporates mixtures of spring mineral water, dried herbs, leaves and/or flowers, plant extracts and oils with non-irritating lipids, binders, surfactants, emulsifiers and preservatives. A "biogenic hydrating water solution" is used as the basis of all moisturizing compositions within the inventive skin care system, with the solution being created by boiling the active ingredients in the spring mineral water, as if making a tea. This differs from other skin care compositions within the prior art in which many of the active ingredients are added in a powdered form to the cream, lotion or other composition.

The inventive system includes a gel mask and topical transport solution, moisturizing lotions, a refresher, and cleansers. The gel mask is a composition comprising ground oats, purified water, lecithin, allantoin, copolymer, extract of licorice, soya extract, and yeast plus thickening agents, binders, preservatives, colorants and the like. It is believed that the gel mask stimulates fibroblast production and is used in combination with a topical transport tea which can be applied by leaning the user's face over a container of the tea after the gel mask has been applied.

The active ingredients of the transport tea which is used to create the biogenic hydrating water complex, and which is used in combination with the gel mask, are leaves, fruits, seeds, roots and flowers. In one embodiment, sodium bicarbonate and extract of licorice are added. The combined ingredients are formed into a tea and the water complex is formed by heating a container of water to a boil, then placing the tea in a strainer in the container of boiling water. After boiling for five minutes, the tea is allowed to steep to create the water complex for use in cleansers and lotions. When used as a transport medium, the container of boiling water is removed from the heat and the tea is allowed to steep so that the beneficial ingredients of the tea are transported by the steam rising from the solution to condense on the user's face and neck. Alternatively, the tea solution may be applied with a wash cloth.

A first embodiment of the moisturizer comprises biogenic hydrating water complex combined with extracts of sugar cane, citrus blossom, pineapple, and licorice, olive, carrot seed and jojoba oils, wheat germ plus emollients, lipids, surfactants, thickeners and preservatives. The refresher comprises distilled water, rose water, chamomile water, jojoba oil, aloe extract, and plantain, which are boiled together, plus panthenol and collagen plus surfactants and preservatives. A first embodiment of the cleanser comprises distilled water in which are boiled powdered oats, sodium laureth sulfate, rose water, wheat germ, and grapefruit oil. Added ingredients are collagen plus additional surfactants, preservatives, lipids and emollients. A second embodiment of the moisturizer comprises biogenic hydrating water complex, aloe, jojoba oil, soy, pineapple extract, almond oil, olive oil, allantoin, kelp, papain, vitamins A, D and E, lecithin, melon oil and extract and tangerine oil and extract. Surfactants, thickeners, emulsifiers and preservatives are added to provide the desired texture and consistency. A second embodiment of the cleanser is made from purified water, aloe vera, jojoba oil, papain, macadamia nut oil, carrot oil, ginseng, kelp, vitamins A and D, citric acid, allantoin, sage, which are combined by boiling in the water then added to surfactants, emulsifiers, thickeners and preservatives. In the second embodiments of the moisturizer and cleanser, the essential oils are included to give the composition a pleasant aroma which can stimulate the user's appetite.

DESCRIPTION OF THE PREFERRED EMBODIMENT

The moisturizers and topical tea of the skin care system of the present invention are generally based upon spring mineral water in which is boiled a tea composition made up of plant components (leaves, flowers, roots and stems) to extract the beneficial qualities of and to combine the active ingredients. For preparation of moisturizers, the resulting tea solution, a "biogenic hydrating water complex", is combined with thickeners, binders, emulsifiers, surfactants, preservatives, lipids and emollients to attain the desired thickness and consistency for a given skin care product. Other active ingredients are natural oils and extracts which are added to the water complex after it is created. Generally the compositions contain at least 20% of the tea solution (water complex) made with spring mineral water.

The cleansers and gel masks of the inventive skin care system are based upon purified water in which is boiled a tea made of dried plant components. The tea solution is then combined with thickeners, binders, emulsifiers, surfactants, preservatives, lipids and emollients to obtain the desired properties.

Representative cosmetic compositions of the present invention include those which are provided in the form of a fluid emulsion, a lotion or a cream.

The biogenic hydrating water complex which serves as the basis for the moisturizers is created from the following ingredients by pulverizing the following ingredient into a tea-like composition. (All ingredients but the water are used to create the topical tea.):

| Biogenic Hydrating Water Complex | |
|---|---|
| Spring Mineral Water | 1 Gallon |
| In which is boiled a tea comprising: | |
| Lavender Spica | 5 tablespoons |
| Lavender Officinalis | 5 tablespoons |
| Lavender Augustifolia | 2 tablespoons |
| Valerian | 2 tablespoons |
| Thyme | 2.5 tablespoons |
| Fenugreek | 4 tablespoons |
| Lecithin | 1 tablespoon |
| Canina Rose Hips | 3 (qty.) |
| Damesca petals | 3 tablespoons |
| Floribunda petals | 3 tablespoons |
| Comfrey | 2 tablespoons |
| Soapwort | 1 tablespoon |
| Primrose flowers | 3 tablespoons |
| Elderflowers | 2.5 tablespoons |
| Birch leaves | 1 tablespoon |
| Parsley | 1 tablespoon |
| Sunflower petals | 3 tablespoons |
| Egyptian Chamomile | 2 tablespoons |
| Roman Chamomile | 2 tablespoons |
| Calendula petals | 3.5 tablespoons |
| Marshmallow leaves | 2 tablespoons |
| Bugle flowers | 1 tablespoon |
| Yarrow flowers | 2 tablespoons |

The above dry ingredients ("tea") are placed in a strainer in a container with one gallon of spring mineral water. The container of water is placed over a heat source and heated to a steady boil (approximately 100° C.) then allowed to continue boiling for 5 minutes. The container is removed from the heat and the tea is allowed to steep for eight additional minutes. The strainer containing the tea is removed from the solution and the solution, the "biogenic hydrating water complex", is allowed to cool. It may be used for creating moisturizers, as described below, or may be stored, refrigerated, for up to seven days.

The spring mineral water for use in the water complex is commercially available under the brand names of Evian® and Pelligrini® which are preferably used in equal portions of one-half gallon each for each batch of the water complex. While the identified brands are preferred, other mineral waters or combinations may be substituted if desired.

The ingredients of the tea are selected for their ability to enhance retention of moisture, vitamins and minerals by the skin. The plants from which the tea is derived are organically grown without pesticides in soil which is prepared with "egg water". ("Egg water" is created by combining one quart of spring mineral water and one quart of purified water into which are placed seven egg shells. The combination is refrigerated at about 40° F. (4° C.) for four (4) days after which the egg shells are removed and the remaining liquid is used to water the soil for one week prior to planting the seedlings and for one week after planting.) This process enriches the soil with vitamins and minerals from the egg water and helps reduce the risk of herbs and flowers from being overcome with insects or disease. The tea ingredients are selected and treated individually to optimize their beneficial qualities, as further described below.

Yarrow (*achilliea millefolium*) flowers are picked just as they bloom and are dried upside-down.

Marshmallow (*althaea officinalis*) leaves are picked from the plant and used fresh for making the tea.

Bugle (*ajuga reptans*) flowers are picked and air dried for one month before use in the tea.

Calendula, also known as marigold (*calendula officinalis*) petals are picked fresh for use in the tea.

Egyptian chamomile (*chamaemelum nobile*) flowers are freshly picked for use in the tea and are effective for softening and removing discoloration from the skin.

Sunflower (*helianthus annus*) petals are freshly picked for used in the tea. (The seeds may be pressed to extract the oil which is used in a moisturizer.)

Three types of lavender, *lavendula augustifolia, lavendula officinalis and lavendula spica*, flowers are used within 49 hours from picking.

Evening primrose (*oenothera biennis*) leaves are used and dried for 72 hours before use in the tea.

Scented geranium (*pelargonium radens, pelargonium crispum, pelargonium capitatum*, and *pelargonium odoratissimum*) stems and flowers are used within 48 hours after picking for inclusion in moisturizers. These help stimulate circulation in the skin.

Parsley (*petroselinum crispum*)leaves are picked and must be dried for 96 hours before they can be used in the tea.

Silver Birch (*betula pendula*)leaves are picked on a stem, dried for 72 hours and added to the tea.

Eiderflower (*sambucus nigra*) flowers are picked and dried for 72 hours.

Primrose (*primula vulgaris*) flower is used freshly picked then soaked in the spring mineral water for 24 hours before the water is boiled.

Roses: Damask and floribunda roses—petals from newly blossomed roses are picked and dried. Pink roses (*canina*) are allowed to overgrow until rose hips are produced. The rose hips are freeze dried and the irritating hairs are removed before adding to the tea.

Soapwort (*caryophyllacea*) root is used by cutting the root to expose the inner flesh. It is also preferable to peel off the outer skin.

Comfrey (*boraginaceae*)leaf is used freshly picked and contains allantoin, a protein that encourages cell division.

Fenugreek (*leguminosae*) seeds are used. Each seed contains 30% protein, lecithin and other vitamins for enriching and softening the skin.

Thyme (*labiatae*) leaf is picked from young plants and dried. Thyme stimulates circulation in the skin to maintain elastin and collagen fibers.

Valerian (*valerianacea*) roots are picked from the plant after it has been erupted from the ground for 96 days (four months).

The above-listed flowers, petals and leaves are left whole for the tea, while the roots and stems are cut to expose their inner flesh. For all ingredients, if they are not used within the specified preparation time, e.g., freshly picked or dried for a set time, they may be freeze dried to preserve their nutrients for later use.

Laboratory tests of the effectiveness of the biogenic hydrating water complex have indicated significant improvement in the elasticity and moisture level of the skin after using the water complex in a skin compress, i.e., placing a cloth soaked in the water complex directly onto the skin. Discolorations resulting from illness or extensive drug therapy were greatly reduced. The biogenic hydrating water complex is believed to enhance water absorption and retention by the skin when applied to the skin either directly by compress, carried to the skin by steam rising from the heated solution, or by incorporation into moisturizers.

The following non-limiting examples illustrate the moisturizers that can be created using the biogenic hydrating water complex according to the present invention.

| Example A - Moisturizer 1 | % by volume |
| --- | --- |
| Biogenic hydrating water complex | 21 |
| Dimethicone | 5 |
| Copolyol | 5 |
| Glycereth 26 | 5 |
| PEG-75 | 5 |
| Orange Blossom Essential Oil* | 5 |
| Sugar Cane Extract | 5 |
| Citrus Blossom Extract (from lemon, orange, apricot and plum) | 2 |
| Wheat Germ | 2 |
| Olive Oil | 2 |
| Carrot Seed Oil | 2 |
| Pineapple Extract | 2 |
| Methyl-Gluceth-20 | 2 |
| Butylene Glycol | 2 |
| Sodium Hyaluronate | 2.5 |
| Retinyl Palmitate | 2 |
| Sodium Glycerhizinate | 2 |
| Extract of Licorice | 2.5 |
| Ginseng | 2.5 |
| Jojoba Oil | 1.5 |
| Hydroxymethyl Cellulose | 1.5 |
| Methylparaben | 1.5 |
| Polysorbate 20 | 1 |
| Propylparaben | 0.5 |
| Butylparaben | 0.5 |

The moisturizer may be in the form of a lotion or creme for application to the skin to moisturize and relieve dryness.

| Example B - Moisturizer 2 | % by volume |
| --- | --- |
| Biogenic Hydrating Water Complex | 25 |
| Aloe | 17 |
| Aloe Vera Gel | 5 |
| Jojoba Oil | 5 |
| Soy | 5 |
| Glycerine | 5 |

| Example B - Moisturizer 2 (continued) | % by volume |
| --- | --- |
| Tangerine Extract and Oil | 5 |
| Pineapple Extract | 4 |
| Almond Oil | 4 |
| Olive Oil | 4 |
| Glycerol Monosterate | 3 |
| Vitamins E, A and D (combined) | 2.5 |
| Emulsifying Wax | 2 |
| Allantoin (comfrey)[1] | 2 |
| Kelp | 2 |
| Papain | 2 |
| Lecithin[1] | 2 |
| Glyceril Monosterate | 2 |
| Coco-Caprate-Caprylate | 1.5 |
| Methylparaben | 1.5 |
| PEG-15 | 1.0 |
| Propylparaben | 1.5 |
| Melon Extract (essential oil) | 1.5 |
| Melon Oil | 1.0 |
| Sweet Almond Oil | 1.0 |
| Mango Oil | 1.0 |
| Propylene Glycol | 1.0 |

[1] These ingredients are in addition to those included in the biogenic hydrating water complex.

Moisturizer 2 was also designed for children undergoing treatment for cancer and other serious illnesses. The essential oils stimulate the appetite, and the melon extract and oil and tangerine extract and oil impart color and pleasant fragrance to the mixture.

While the cleansers and gel mask do not incorporate the biogenic hydrating water complex, they are, nonetheless, based upon a tea solution which is created by boiling certain plant components in water. An asterisk (*) indicates an ingredient that is incorporated into the composition by boiling it in the specified water to create a tea solution. All ingredients that are added after the tea solution is created are not indicated with an asterisk.

| Example C - Mask | % by volume |
| --- | --- |
| Purified Water | 30 |
| Ground Oats* | 30 |
| Lecithin* | 10 |
| Allantoin* | 6.5 |
| Copolymer | 5.5 |
| Extract of licorice* | 4 |
| Soya Extracts*[1] | 3 |
| Yeast* | 2.5 |
| Xanthan Gum | 2.5 |
| Propylparaben | 2.5 |
| Tocopherol Acetate | 2.0 |
| Titanium Dioxide | 1.0 |
| Iron Oxides | 0.5 |

[1] Soya extract is approximately 9 parts soybean extract and one part almond oil.

The mask is in the form of a gel which is applied to the skin and used in combination with the biogenic hydrating water complex or transport tea described below.

| Example D - biogenic hydrating water complex | % by volume |
| --- | --- |
| Water | ** |
| Senna* | 12 |
| Fennel* | 9 |

Example D - biogenic hydrating water complex

| | % by volume |
|---|---|
| Ginseng* | 6 |
| Lemon and Orange Rind* | 6 |
| Basil* | 6 |
| Parsley* | 6 |
| Oregano* | 6 |
| Anise* | 3 |
| Caraway Seed* | 3 |
| Dandelion* | 3 |
| Peach Wedges* | 3 |
| Lemon Verbeena* | 3 |
| Lavender* | 3 |
| Lilac* | 3 |
| Chamomile* | 3 |
| Marjoram* | 3 |
| Raspberry Leaves* | 3 |
| Birch Leaves* | 3 |
| Rose Hips* | 3 |
| Peppermint Leaves* | 2 |
| Rose Petals* | 2 |
| Rosemary* | 2 |
| Thyme* | 2 |
| Sage* | 2 |
| Baking Soda(sodium bicarbonate)* | 1.8 |
| Licorice Root* | 1.5 |
| Green Tea* | 1.5 |
| Yarrow Flowers* | 1.5 |
| Extract of Licorice* | 0.2 |
| Centaury* | 0.2 |
| Blackberry* | 0.1 |

(**The dry tea is combined in the above proportions then added to boiling water, on the order of 2-3 cc of dry tea per ½ to 1 liter water, boiled for four minutes, removed from the heat, then steeped for five minutes to release the effects of the ingredients with the steam rising from the water.)

The either embodiment of the biogenic hydrating water complex may be used in combination with the mask, causing the mask to retain the droplets containing the transport tea against the skin. An important active ingredient of the second embodiment of the water complex or transport tea is baking soda (sodium bicarbonate) which enhances the release of the vitamins and other beneficial components in the herbs, flowers and fruit extracts and oils. The baking soda is most active during the first 45 seconds following introduction of the dry mixture into the steaming water. The extract of licorice is also an important factor in enhancing the effectiveness of the treatment since extract of licorice is a natural histamine and acts as a vasodilator to expedite the absorption into the skin of the treatment's beneficial elements. The combined treatment of the mask and water complex or transport tea has provided improved facial tone, increased circulation to the face, improving the user's facial color, and enhances the skin's responsivity to topical creams and moisturizers that can seal moisture into the skin. This treatment addresses a problem that is very common amongst cancer and AIDS patients, and other persons using chemicals and medicines on a long term basis. affect the combined treatment of the mask and transport tea, the user places the mask over the face then adds the dry tea to hot water in an open container while leaning over the container. Steam rises from the water, causing moisture to condense on the skin. Alternatively, the tea can be allowed to soak for approximately 4 minutes then can be applied with a cloth or similar applicator.

| Example E - Refresher | |
|---|---|
| | % by volume |
| Purified Water | 40 |
| Rose Water* | 10 |
| Chamomile Water* | 10 |
| Panthenol | 9 |
| Collagen | 3.5 |
| Jojoba Oil | 8 |
| Aloe Extract | 9 |
| Plantain* | 2.5 |
| Glycerine | 2.5 |
| Sodium Borate | 2 |
| PEG-60 | 1.5 |
| Benzoic Acid | 1.5 |
| Methylparaben | 1 |

The refresher is in a liquid form and may be applied by spraying onto the skin or by using an applicator cloth or pad. The refresher removes the last traces of the mask that may be left on the skin and restores the skin's natural pH balance.

| Example F - Cleanser 1 | |
|---|---|
| | % by volume |
| Purified Water* | 36.5 |
| Sodium Laureth Sulfate | 10.0 |
| Rose Water* | 8.0 |
| Wheat Germ* | 5.0 |
| Grapefruit Oil | 5.0 |
| Lauramide DEA | 5.0 |
| PEG-32 | 4.5 |
| Sodium Cocysarcosinate | 4.5 |
| Glycerine | 4.5 |
| Steareth-20 | 4.0 |
| Copolymer | 3.5 |
| Laneth-16 | 2.5 |
| Propylene Glycol | 1.0 |
| Cetyl Alcohol | 0.5 |
| Methylparaben | 0.5 |
| Butylparaben | 0.5 |
| Propylparaben | 0.5 |

Cleanser 1 is in the form of a gel which foams as it is activated by applying water to gently exfoliates and deep cleanse. It is also effective as a make-up remover.

| Example G - Cleanser 2 | |
|---|---|
| | % by volume |
| Purified Water* | 40.0 |
| Aloe Vera* | 14.0 |
| Jojoba Oil* | 5.0 |
| Papain* | 5.0 |
| Macadamia Nut Oil | 5.0 |
| Cocamide Betaine Propyl[1] | 5.0 |
| Sodium Laureth Sulfate | 5.0 |
| Caprylic coco triglyceride[2] | 3.5 |
| Cocol DEA | 3.5 |
| Carrot Oil | 3.0 |
| Ginseng* | 3.0 |
| Kelp* | 2.0 |
| Vitamin A | 1.5 |
| Vitamin D | 1.5 |
| Citric Acid* | 1.5 |
| Allantoin (comfrey)* | 1.0 |
| Sage* | 1.0 |
| Methylparaben | 1.0 |
| Propylparaben | 1.0 |
| Triethanolamine | 0.5 |

[1] The Cocamide Betaine Propyl is a combination in equal parts of oil from the coconut kernel, beet juice extract, and propyl gallate. The coconut kernel oil is a saturated fat which is an excellent source of sealing moisture in the skin. The betaine is from juice extracted from a beet after the beet has been placed in a pot of boiling water which is then removed from the heat source, allowing the beet to simmer for five minutes. The juice from the beet is an excellent source for treating muscle weakness and has no known toxicity or side effects. Propyl gallate is a white powder that acts as an anti-oxidant which helps control the dehydration process that occurs in the cells during prolonged exposure to chemotherapy drugs, radiation treatments and other intensive drug regimens. The cocamide betaine propyl complex helps balance the fat content of the coconut oil.

[2] The Caprylic-coco triglyceride complex comprises glycerine and caprylic, capric and lauric acids used in equal part. This complex is an emollient which prevents early water loss from the skin.

Cleanser 2 was developed for children undergoing treatment for cancer or other serious illnesses. It is believed that the essential oils in the composition provide an aroma therapy which stimulate the child's appetite to assist in the recovery process.

The various texturizers, emulsifiers, surfactants, lipids, emollients and preservatives which are listed but not specifically discussed are known in the art such that the purpose for inclusion and the selection of a particular combination of these ingredients would be apparent to one skilled in the art. Thus, no further discussion of these ingredients is deemed necessary.

The skin care system of the present invention addresses the specific concerns of individuals who are undergoing intensive therapy for serious illnesses where the therapy itself has side effects which can cause significant dryness and heightened sensitivity in the individual's skin. Although this system was developed for such individuals, it is equally appropriate for use by persons who are healthy but desire natural, non-irritating skin care products.

It will be evident that there are additional embodiments which are not illustrated above but which are clearly within the scope and spirit of the present invention. The above description and drawings are therefore intended to be exemplary only and the scope of the invention is to be limited solely by the appended claims.

I claim:

1. A method for improving moisture-absorption and retention in a person's skin, the method which comprises:

creating a tea solution comprising the steps of:
heating a container of spring mineral water to a boil over a heat source;
combining a plurality of plant components comprising flowers, petals, plant stems, plant leaves, plant roots and plant seeds in the respective quantity in tablespoons per one gallon of said spring mineral water of lavender flower—12, valerian root—2, thyme leaf—2.5, fenugreek seed—4, rose petal—6, comfrey leaf—2, soapwort root—1, primrose flower—3, elderflower flower—2.5, birch leaf—1, parsley leaf 1, sunflower petal—3, chamomile flower—4, calendula petal—3.5, marshmallow leaf—2, bugle flower—1 and yarrow flower—2 to form a tea composition, wherein each plant from which said plurality of plant components is obtained is grown in a soil enriched by adding water containing vitamins and minerals;
placing a strainer containing said tea composition in said container of boiling water and boiling said tea composition;
removing said container from said heat source and steeping said tea composition in said spring mineral water to create a tea solution;
removing said tea composition from said tea solution; and
applying said tea solution to said person's skin.

2. A method as in claim 1 wherein the step of applying said tea solution further comprises combining said tea solution with at least one ingredients selected from the group consisting of emulsifiers, thickeners, emollients, lipids and preservatives to form a skin lotion.

3. A method as in claim 1 wherein the step of applying said tea solution comprises placing a compress on said person's skin.

4. A method as in claim 1 wherein the step of applying said tea solution to said skin comprises placing said person's skin over said container so that steam rising from said tea solution comes in contact with said person's skin.

5. A method as in claim 1 wherein the vitamins and minerals added to said soil are contained within a mixture containing mineral water and egg shells, said mixture being used to water said soil.

6. A base solution for a cosmetic composition improving moisture-absorption and retention in a person's skin, the base solution which comprises:

spring mineral water;
a tea contained within a strainer, said tea comprising a plurality of plant components comprising flowers, plant stems, plant leaves, plant roots and plant seeds in the respective quantity in tablespoons per one gallon of said spring mineral water of lavender flower—12, valerian root—2, thyme leaf—2.5, fenugreek seed—4, rose petal—6, comfrey leaf—2, soapwort root—1, primrose flower—3, elderflower flower—2.5, birch leaf—1, parsley leaf 1, sunflower petal—3, chamomile flower—4, calendula petal—3.5, marshmallow leaf—2, bugle flower—1 and yarrow flower—2, wherein each plant from which said plurality of plant components is obtained is grown in a soil enriched by adding vitamins and minerals;
wherein said spring mineral water is heated to a boil over a heat source and said strainer is disposed within said spring mineral water, said spring mineral water is removed from the heat source and said tea is steeped in said spring mineral water then removed to create a tea solution.

* * * * *